US008269953B2

(12) United States Patent
Bado et al.

(10) Patent No.: US 8,269,953 B2
(45) Date of Patent: Sep. 18, 2012

(54) SPECTROSCOPIC DETECTOR AND METHOD FOR DETERMINING THE PRESENCE OF BLOOD AND BIOLOGICAL MARKER SUBSTANCES IN LIQUIDS

(75) Inventors: Itka Bado, Bad Homburg (DE); Michael Herrenbauer, Neu-Anspach (DE); Ulrich Moissl, Bad Vilbl (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 0 days.

(21) Appl. No.: 13/241,428

(22) Filed: Sep. 23, 2011

(65) Prior Publication Data

US 2012/0062869 A1 Mar. 15, 2012

Related U.S. Application Data

(63) Continuation of application No. 12/306,088, filed as application No. PCT/EP2007/005631 on Jun. 26, 2007, now Pat. No. 8,054,452.

(30) Foreign Application Priority Data

Jun. 29, 2006 (DE) .......................... 10 2006 029 899

(51) Int. Cl.
*G01N 33/48* (2006.01)
(52) U.S. Cl. ........... 356/39; 356/246; 356/440; 356/445
(58) Field of Classification Search ............... 356/39–42, 356/73, 244, 246, 436, 440; 422/82.05, 82.09; 250/428–438, 373, 576, 288.5; 435/288.5, 435/36, 43, 61, 64, 69; 73/36, 43, 61, 64, 73/69
See application file for complete search history.

(56) References Cited

U.S. PATENT DOCUMENTS 3,840,304 A 10/1974 Hirafuji
4,181,610 A 1/1980 Shintani et al.
(Continued)

FOREIGN PATENT DOCUMENTS

DE 69501590 8/1998
(Continued)

OTHER PUBLICATIONS

International Preliminary Report of Patentability and Written Opinion from PCT/EP2007/005631, dated Jan. 13, 2009.

*Primary Examiner* — Tarifur Chowdhury
*Assistant Examiner* — Michael P Lapage
(74) *Attorney, Agent, or Firm* — Kenyon & Kenyon LLP

(57) ABSTRACT

The invention relates to a detector for measuring scattered light in liquids having a housing, a transparent, flexible tube for transporting liquid through the housing, a light emitter, and a light detector. Two parallel surfaces are formed in the housing, between which the tube is arranged such that two opposing tube walls are formed in a planar parallel manner. The light emitter is arranged in such a way that the optical axis thereof is perpendicular to the parallel surfaces of the first tube wall, and the light detector is adjacent to the light emitter, the optical axes of the light emitter and light detector forming an angle smaller than 90°. The invention also relates to a method for detecting the presence of blood and for the quantitative determination of biological marker substances, especially bilirubin, in solution, and to a device for treating blood containing the detector.

19 Claims, 7 Drawing Sheets

U.S. PATENT DOCUMENTS

| | | | |
|---|---|---|---|
| 4,227,814 A | 10/1980 | Soodak et al. |
| 4,500,793 A | 2/1985 | Kuramoto |
| 4,533,350 A | 8/1985 | Danby et al. |
| 4,673,820 A | 6/1987 | Kamen |
| 4,745,279 A | 5/1988 | Karkar et al. |
| 5,061,632 A | 10/1991 | Shepherd et al. |
| 5,331,958 A | 7/1994 | Oppenheimer |
| 5,385,539 A | 1/1995 | Maynard |
| 5,565,977 A | 10/1996 | Rosinko |
| 5,601,080 A | 2/1997 | Oppenheimer |
| 5,644,402 A | 7/1997 | Chevallet |
| 5,773,301 A | 6/1998 | Ziegler |
| 5,783,826 A | 7/1998 | Meunier |
| 6,103,197 A | 8/2000 | Werner |
| 6,223,069 B1 * | 4/2001 | Pfeiffer et al. ............ 600/431 |
| 6,510,330 B1 | 1/2003 | Enejder |
| 6,678,052 B1 | 1/2004 | Hanagandi et al. |
| 6,718,190 B2 | 4/2004 | Krivitski et al. |
| 6,806,947 B1 | 10/2004 | Ekdahl et al. |
| 2006/0243031 A1 | 11/2006 | Kondo et al. |

FOREIGN PATENT DOCUMENTS

| | | |
|---|---|---|
| EP | 0231652 | 8/1987 |
| EP | 0575712 A2 | 12/1993 |
| EP | 0818682 | 1/1998 |
| EP | 1083948 B1 | 3/2001 |
| GB | 1320533 | 6/1973 |
| WO | 0033053 A1 | 6/2000 |
| WO | 2004/057313 A1 | 7/2004 |

* cited by examiner

SPECTROSCOPIC DETECTOR AND METHOD FOR DETERMINING THE PRESENCE OF BLOOD AND BIOLOGICAL MARKER SUBSTANCES IN LIQUIDS

CROSS REFERENCE TO RELATED APPLICATIONS

This application is a continuation of U.S. patent application Ser. No. 12/306,088, filed on Dec. 22, 2008, which is a 371 national phase application of PCT/EP2007/000433 filed Jun. 26, 2007, claiming priority to German Patent Application No. 10 2006 029 899.3 filed Jun. 29, 2006.

FIELD OF INVENTION

The invention concerns a detector and the detection of blood and biological marker substances in optically dense and clear liquids or in secondary liquids used in blood purification machines.

BACKGROUND OF THE INVENTION

To ensure patient safety, a blood detector must be used when using a membrane filter for blood purification to prevent critical patient conditions caused by risks such as possible blood loss, membrane rupture of the filter, mistaking of connections or hemolysis.

Spectroscopic analyses for determining blood and biological marker substances in solution are known from the prior art. EP 0 575 712 A2 describes the spectroscopic analysis of blood on a squeezed tube in dialysis and measurement in transmission. EP 1 083 948 B1 describes the spectral measurement of waste products in dialysis liquid, whereby the measurement is performed directly in the dialysis liquid discharged during dialysis treatment. The measurement is performed by spectral photometry and the measured value obtained is multiplied by the flow volume of dialysis liquid. The measurement is performed in transmission.

U.S. Pat. No. 5,644,402 describes an optical detector for blood recognition in blood treatment appliances, in which the transmission behavior of the arrangement to be measured is measured by multiple crossing of the medium measured. U.S. Pat. No. 6,718,190 B1 discloses a transmission analysis with inclined optical axes. WO 2004/057313 describes optical measurements in a squeezed tube, whereby different light sources and sensors and non-inclined optical axes are used.

However, optical transmission measurements are not possible or are imprecise, especially in optically dense solutions. Here, the question arises how certain components in the liquid are to be determined with sufficient accuracy. It may also be necessary to recognize blood in secondary liquids so as to determine a blood leak in the blood purification unit (e.g. dialysis machine).

SUMMARY OF THE INVENTION

One aspect of the present invention is to provide a detector for detection of blood in a secondary circuit flowing over the filter and containing an optically dense suspended solution. It should also be possible, where appropriate, to detect blood, especially in an optically clear solution.
In addition, another aspect of the present invention is to control therapeutic progress and determine the time for ending the therapy or the need for adsorber replacement by quantitative determination of certain marker substances (e.g. bilirubin in liver support therapy). The detector should also permit the principal distinction between an optically clear and an optically dense solution.

The present invention provides a detector for measuring stray light in liquids, comprising a casing, a light-transmissive, flexible tube for transporting liquids conducted through the casing, a light emitter, and a light detector. Two essentially flat surfaces are formed by the casing, between which surfaces the tube is arranged such that two juxtaposed tube walls are formed to be essentially flat. The light emitter with its optical axis is arranged to be perpendicular to the flat surfaces beside the first tube wall and adjacent to said first tube wall, whereby the optical axes of the light emitter and light detector form an angle that is smaller than 90°.

According to a preferred embodiment, the flat surfaces of the tube walls are arranged parallel to each other. It may be sufficient for the flexible tube for transporting liquids to have only the tube wall adjacent to the flat surface be flexible, while the other defining walls of the tube may be rigid. In general, however, the entire tube will be flexible.

The light emitter radiates light in a broad wavelength range through a shutter onto the tube at a perpendicular angle. A white LED is preferably used as the light source with wavelengths in the range from approximately 400 to 700 mm. The tube is preferably a standard tube as used in dialysis. A disposable tube is preferred.

Since the light emitter with its optical axis is arranged to be perpendicular to the flat surfaces beside the first tube wall, optimal passage of the light into the interior of the tube is ensured.

The detector according to the present invention can also be used in optically dense liquids. According to the present invention, an optically dense liquid is defined as a light-impermeable liquid. An optically clear liquid is defined as a liquid with high transmission of visible light. Light-transmissive is defined where at least a part of the radiated light can permeate the entire tube diameter and the liquid contained in the tube, when the light is radiated from one side of the tube. In light-impermeable liquids, virtually no light passes through the tube diameter and the liquid contained in the tube, i.e. transmission does not occur. According to the present invention, the term "liquid" refers in particular to solutions and suspensions.

In a first embodiment, the light passes through the transparent tube wall into the optically dense liquid in the tube interior and is absorbed or partly diffused, depending on the given wavelength. An optically dense liquid is, for example, an optically dense suspension or optically dense solution. The optical density of the fluid prevents transmission through the interior of the liquid, so that no reflection on the rear tube wall facing away from the light emitter or on the rear casing wall, on which the rear tube wall abuts, takes place.

In a second embodiment, the light passes through the first transparent tube wall into the optically clear liquid in the tube interior. In this case, however, at least a part of the light permeates the optically clear liquid present in the entire tube diameter in the tube interior and is reflected in a preferred embodiment on the rear tube wall and/or rear casing wall facing away from the light emitter. The rear casing wall is the wall in the interior of the casing on which the rear tube wall abuts. In the case of an optically clear solution, the reflected light volume is lower than the radiated light volume, since the light passes through the liquid twice.

The light detector is preferably located with its optical axis at an angle of 45° to the optical axis of the light emitter. The light detector absorbs the reflected or diffused light and analyzes the signal. The light detector preferably comprises a light conductor that absorbs the light and a spectrometer connected with the light conductor. The light is, for example, conducted over a light-wave conductor into a micro-spectrometer, in which the wavelength spectrum is absorbed.

In an especially preferred embodiment, the intersection of the optical axes of the light emitter and light detector is located precisely on the media boundary between the tube wall facing the light emitter/light detector and the liquid in the tube. Depending on the density of the solution, however, the intersection may also be located a few tenths of a millimeter behind the media boundary in the liquid in the tube interior. In a further advantageous embodiment, the intersection of the optical axes of the light emitter and light detector is therefore located in an area extending from the media boundary between the tube wall facing the light emitter/light detector and the liquid transported in the tube up to 0.5 mm into the tube interior.

As described above, after passing through the entire tube diameter, light is reflected on the rear tube wall facing away from the light emitter and/or the rear casing wall. To improve the light reflection in this case, a reflecting surface is provided preferably on the side of the tube facing away from the light emitter and light detector. The reflecting surface can be either a reflecting tube surface or a reflecting casing surface or both. To achieve a reflection, aluminum, for example, is a suitable casing material. The casing is otherwise preferably made of plastic. For simple insertion of the tube in the casing, it is advantageous to provide a lid on the rear side facing away from the light emitter and light detector.

Preferably at least one of the two casing walls (the casing wall facing the light emitter and the casing wall facing away from the light emitter) is arranged to be flat, so that the tube wall is in flat formation when inserted in the casing. According to a preferred embodiment, which is used especially in double transmission, both casing walls are arranged to be flat and parallel with each other, so that the layer thickness within the inserted tube to be radiated is substantially parallel and consequently constant.

A light-transmissive glass pane may be disposed between the tube and the light emitter and the light detector to prevent contamination of the light emitter and/or light detector openings in the casing (e.g. in the event of a tube leakage). This glass pane can preferably be arranged parallel to the opposite lid surface.

The light is preferably radiated into the solution through a 2-4 mm wide opening (shutter), whereby the system is made relatively insensitive to divergences of the bore holes in the casing construction or of tube thickness within the fault tolerance range.

If hemoglobin reaches the detector, light absorption increases and the reflected light volume simultaneously diminishes correspondingly at specific wavelengths depending on the substance. The signal change compared to the previously determined reference signal for these wavelengths, for which the light reflection of the pure suspension or solution is measured, results in a signal deflection for blood that then actuates a blood alarm, under application of an algorithm defined below, when a defined alarm criterion is fulfilled. The same measuring system can also be used quantitatively for other substances whose spectral maxima are not overlaid by interfering substances.

For signal analysis, the light detector advantageously comprises an analysis unit. The analysis unit calculates a wavelength-dependent signal change $\Delta S$ from a wavelength-dependent measuring signal and a likewise wavelength-dependent reference signal in accordance with the following formula (1):

$$\Delta S(\lambda) = \Delta S = \log\left(\frac{I(\lambda)_{referencevalue}}{I(\lambda)_{measuredvalue}}\right) \quad (1)$$

$\lambda$ = wavelength, $I$ = intensity

The analysis unit then generates a convolution integral, beginning with a wavelength $\lambda_0$ of the signal change function $\Delta S(\lambda)$ over a defined wavelength range, e.g. from $\lambda_0$ to $\lambda_1$. The convolution function according to (2) is e.g.:

$$\psi(x) = \left(\frac{a}{\sqrt{b}}(\pi)^c\right) \cdot \left(d - \left(\frac{x}{j}\right)^f\right) \cdot e^{-\frac{(\frac{x}{j})^g}{h}} \quad (2)$$

where $x=\lambda-\lambda_0$ and a, b, c, d, f, g, h and j are selected constants.

For every wavelength, the signal change function $\Delta S$ is multiplied with the convolution function $\psi(x)$. Then the convolution integral for the wavelength $\lambda_0$ is calculated from the sum of all products. If no blood is in the medium, the convolution integral should be zero where possible, regardless of all interfering influences. In the case of blood, however, it becomes positive. The value thus obtained is compared with a number of defined alarm criteria. If one of the criteria is fulfilled, blood is recognized.

To ensure that the spectra divergence at differential oxygen saturations has no effect on the convolution integral, $\lambda_0$ (preferably $\lambda_0$=558 nm) is so selected that the signal strengths of blood saturated with oxygen and blood unsaturated with oxygen are equal for this wavelength.

Two different analysis methods may be used for evaluation. For determination of substances such as e.g. bilirubin, the signal $\Delta S(\lambda)$ is used for a particular wavelength. On the other hand, to permit recognition of blood despite differential blood saturation levels, a convolution integral is again used. The signal change function $\Delta S(\lambda)$ is thereby multiplied for every wavelength by a pre-selected convolution function $\psi(x)$ and the product added up.

The apparatus according to the invention can also be used to examine the functions of the detector arrangement, whereby the presence of blood in the measured object is simulated.

For this purpose, both a white radiating and green radiating LED are used as light emitters. Two measurements are performed in sequence, whereby preferably both LEDs radiate in the first measuring step, and only the white LED radiates in the second measuring step. By switching off the green LED, blood in the tube is simulated because the hemoglobin present in the tube is absorbed inter alia in the green wavelength range, so that less light reaches the detector in this wavelength range.

To test functionality, the signal change is determined according to a changed version of equation (1), i.e. according to equation (3):

$$\Delta S(\lambda) = \log\left(\frac{I(\lambda)_{LED\ white\&green}}{I(\lambda)_{LED\ white}}\right) \quad (3)$$

For the signal value $I(\lambda)_{LED\ white}$, a saved reference value can advantageously also be used.

The same function is then used accordingly for the spectra analysis for blood, and the signal value so obtained is compared with a control value. If the detector is functioning properly, the signal value should thereby always be higher than the control value. If this is not the case, this indicates a malfunction of the detector. This simulation can, incidentally, be performed both in an optically clear and an optically dense solution.

According to a further embodiment, air recognition in an optically dense solution is also possible. If air enters the secondary circuit tube, this lowers the intensity of the spectrum measured. This is because air is very similar to an optically transparent solution, whereby only a part of the reflected light reaches the detector due to the arrangement of the optical system, as in the case of the optically transparent solution.

In a further aspect, the present invention concerns a process for the detection of blood and quantitative determination of biological marker substances, in particular bilirubin, in solution, whereby the process steps previously described for the analysis unit are performed. The detection of bilirubin with the detector according to the present invention is particularly useful in liver support therapy for control of therapeutic progress and determination of the time for ending the treatment or replacing the adsorber.

In a further aspect, the present invention accordingly also concerns the use of the detector according to the invention for the detection of blood, in particular hemoglobin, and of biological marker substances, in particular bilirubin.

Finally, the present invention also concerns an apparatus for blood treatment with a blood treatment unit, a blood circuit connected with the blood treatment unit and a secondary liquid circuit likewise connected with the blood treatment unit. The secondary liquid circuit is preferably a dialysis liquid circuit. The secondary liquid circuit comprises a tube system and a detector as described above, through which the tube of the secondary liquid circuit is laid.

The present invention is described in detail below by reference to preferred embodiments. These specific embodiments only serve for clarification and are not intended to limit the invention described in general above.

DETAILED DESCRIPTION OF THE DRAWINGS

Figure 1:
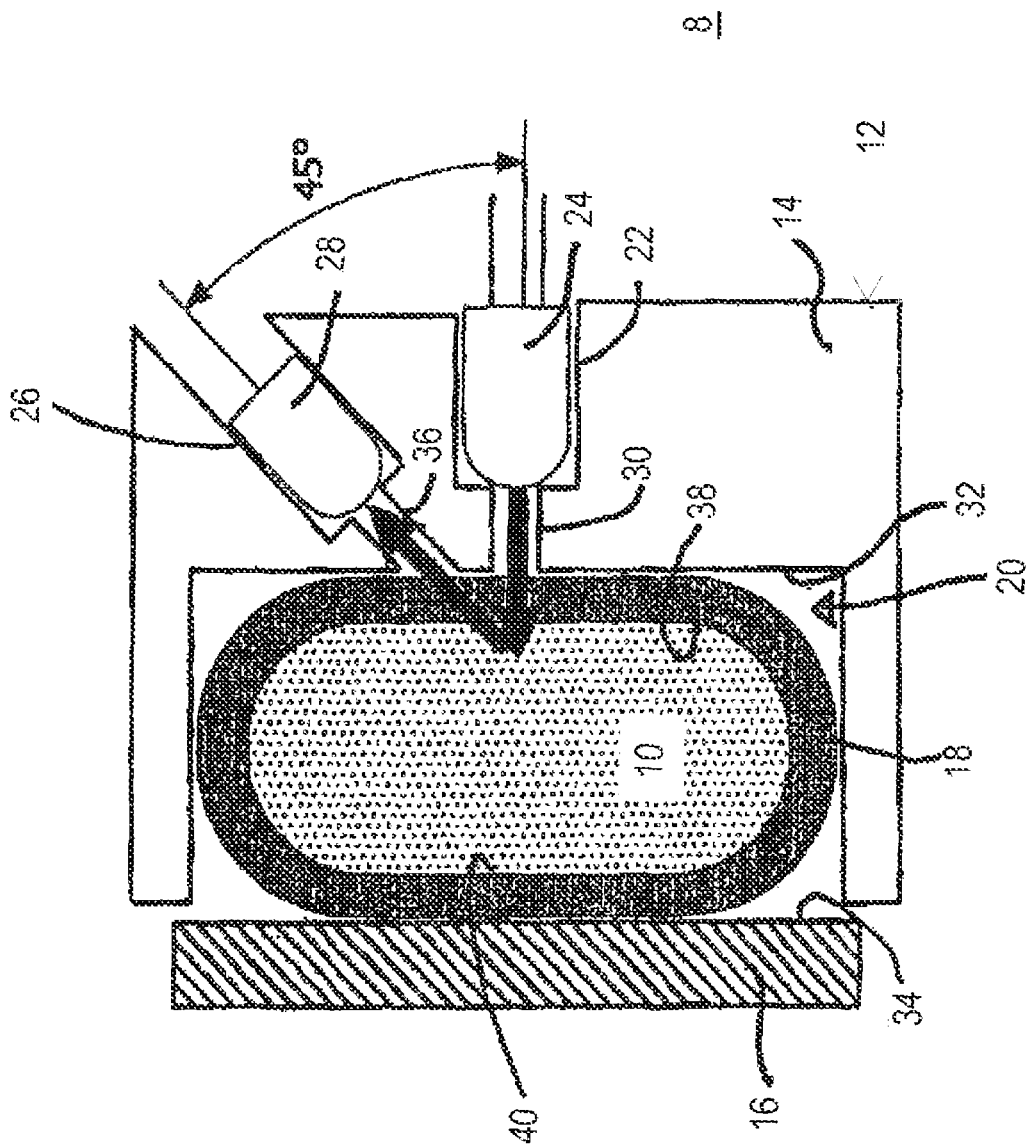
FIG. 1 shows a first embodiment of the detector according to the present invention in cross-section, whereby a measurement in optically dense solution is shown.

FIG. 1 shows a first embodiment of the detector 8 according to the invention in a view diagonal to the flow direction of the liquid 10. A casing 12 is formed by a main casing part 14 and a casing lid 16, which serves for simple insertion of a tube 18 into the casing 12 and as a measuring background. When tube 18 is inserted, the casing lid 16 is fastened with tightly sealing effect on the main casing part 14.

The main casing part 14 further comprises a channel 20 for guiding tube 18 through casing 12, a first recess 22 for mounting a light emitter 24 and a second recess 26 for mounting a light detector 28. Both recesses 22 and 26 open from the outside of the main casing part 14 and extend over a narrowed first shutter 30 for the ray beam of light emitter 24 and a second narrowed shutter 36 for the ray beam of light detector 28 and then through the main casing part 14 to end in the channel 20.

The light emitter 24 is advantageously a light source emitting white light, preferably an LED emitting white light.

According to a further embodiment, the light emitter 24 may consist of two light sources where necessary, which emit different light spectra, e.g. a light source emitting white light and a light source emitting green light, in particular in the form of an LED arrangement.

Tube 18 is guided through casing 12, whereby liquid 10 can be conducted through the tube 18. The tube itself is permeable by the light emitted by light emitter 24.

The flat inner surface 34 of the casing lid 16 is advantageously arranged in parallel with the opposite flat channel surface 32 of the main casing part 14, whereby both surfaces 32, 34 are defining surfaces for the inserted tube 18. The distance between the two surfaces 32 and 34 is thereby smaller than the outer diameter of the tube 18. This arrangement deforms the flexible tube 18 after insertion in the casing 12 so that the initially round form is transformed into a substantially oval form with two almost flat and preferably planar parallel tube walls 38, 40.

The light detector 28 is adjacent to the first channel surface 32, whereby a light channel extending from channel 20 through the main casing part 14 is formed here by a second shutter 36 together with the second recess 26. This light detector 28 is positioned adjacent to the light emitter 24, whereby the optical axes extending through the two shutters 30 and 36 and through the first and second recesses 22 and 26 advantageously form an angle of approximately 45°. In FIG. 1, the optical axes that also represent the light beams, are shown as arrows extending from light emitter 26 and light detector 28, which intersect at the media boundary between the first tube wall 38 and the liquid 10 or a few tenths of a millimeter behind the media boundary within the liquid 10.

In accordance with its first embodiment, the light detector 28 itself is formed as a light conductor, which may be connected with a spectrometer for further processing of the light signal, or formed as a light diode or the like according to a second embodiment, which can directly convert the irradiated light volume into an electrical measuring signal.

FIG. 1 presents the measurement in optically dense liquid, whereby it is sufficient if only the first casing wall 32 is flat, so that, where suitable, a flat arrangement of the rear casing wall 34 is not necessary. The liquid 10 here is, for example, an optically dense solution or suspension. The light penetrates through the first tube wall 38 into the solution 10, where it is partly absorbed and partly diffused depending on the wavelength. Due to the optical density in the liquid 10, any transmission through the liquid 10 is prevented, so that reflection on the second tube wall 40 or the inner surface 34 of the lid 16, on which the second tube wall 40 abuts, does not occur. In schematic presentation, this drawing merely shows the partial diffusion on the liquid surface in the direction of the light detector 28 in the form of an arrow directed towards light detector 28.

Figure 2:
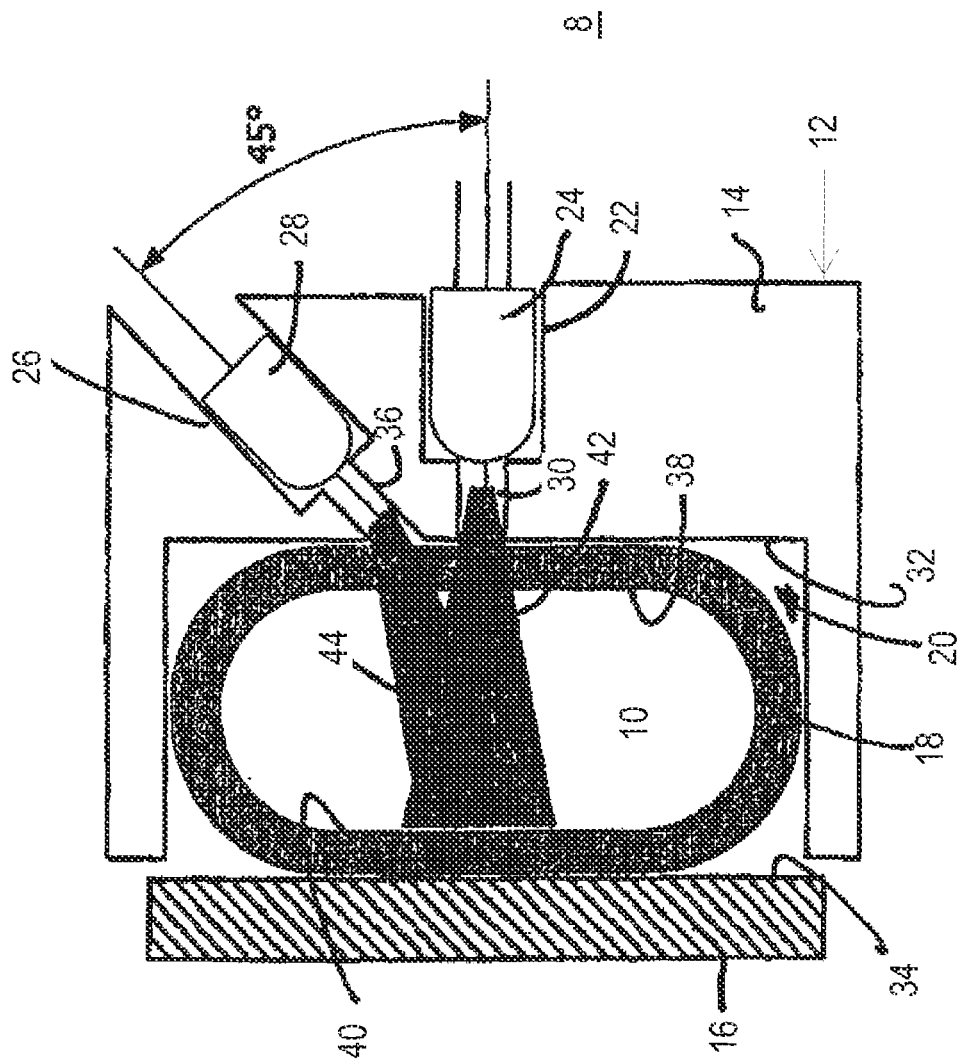
FIG. 2 shows the embodiment of the detector according to FIG. 1 performing a measurement in optically clear solution.

FIG. 2 shows the exemplary embodiment of the detector according to FIG. 1, with an optically clear solution as liquid 10. The light 42 emitted by light emitter 24 penetrates the first tube wall 38 and the entire liquid 10 present in the tube and is then reflected on the second rear tube wall 40 and/or the inner surface 34 of the lid 16. A part 44 of the reflecting light again penetrates the entire liquid and is then absorbed by the light detector or light conductor 28. According to this embodiment, it is advantageous if the rear casing wall 34 is parallel to the front first casing wall 32.

Figure 3A:
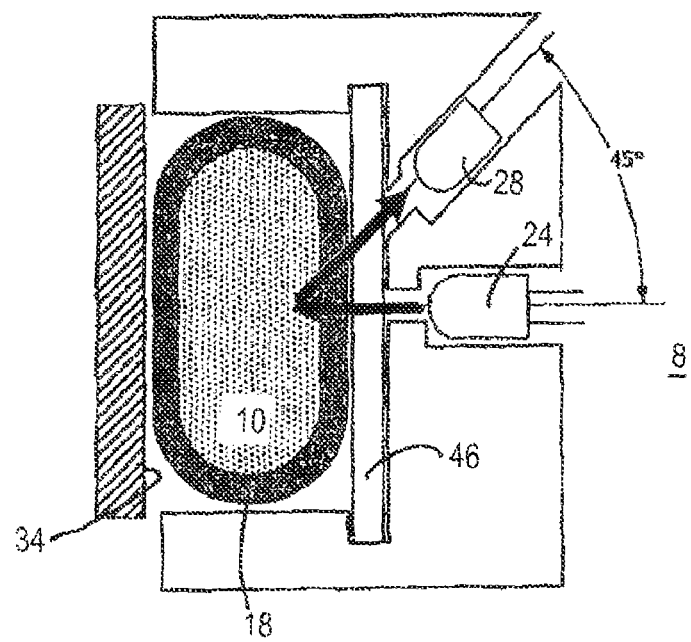
FIG. 3a shows a second embodiment of a detector according to the present invention in cross-section performing a measurement in optically dense solution with a light emitter.

FIG. 3a shows a second embodiment of the detector 8 in cross-section in a measurement in optically dense solution. In contrast to the embodiment shown in FIGS. 1 and 2, a glass pane 46 which is permeable to the irradiated light is arranged between the first tube wall 38 and the surface 32. This prevents possible contaminations of the light emitter or light detector openings in the casing 12. The rear casing wall 34 is advantageously arranged parallel to the glass pane 46.

Figure 3B:
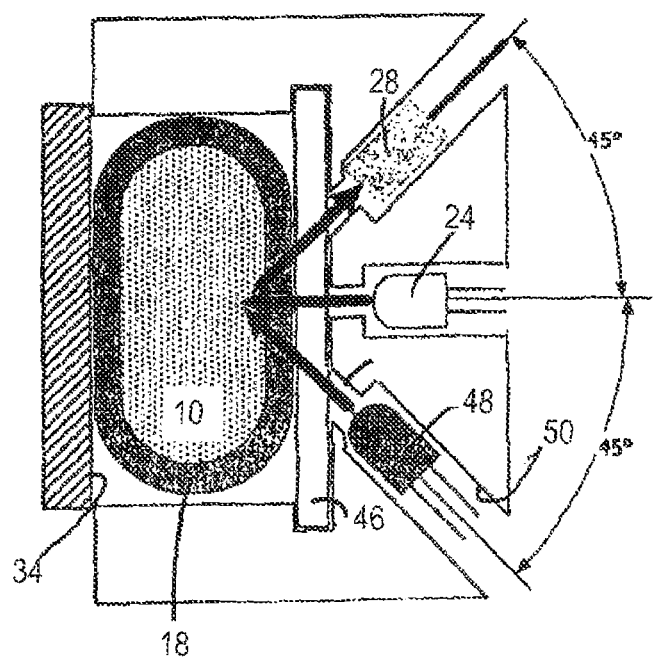
FIG. 3b shows the embodiment of FIG. 3a with two light emitters.

FIG. 3b shows a further embodiment with two light emitters of different irradiation wavelengths (e.g. green). In addition to the first light emitter 24, there is a second light emitter 48, which is mounted in a third recess 50 in the main casing part 14. The recess 50 opens from the outside of the main casing part 14 and extends over a further narrowed third shutter 52 for the ray beam of the light emitter 48 through the main casing part 14 and also ends in channel 20. The light beam and the optical axis of the second light emitter 48, as indicated by the arrows in FIG. 3a, advantageously form an angle of 45° with the axis of the first light emitter 24, whereby other angles are also possible and merely depend on the volume geometry of the light emitters or detectors used. The two axes intersect at the media boundary between the first tube wall 38 and the liquid 10 or a few tenths of a millimeter behind the media boundary within the liquid 10.

Figure 4:
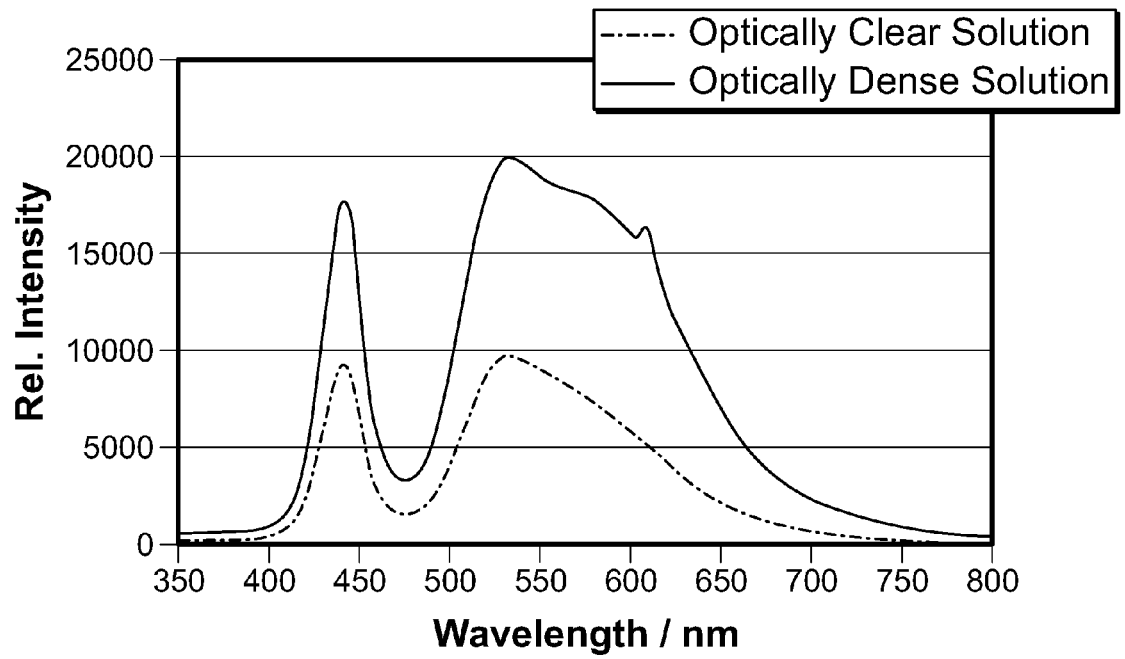
FIG. 4 shows a comparison of the measuring signal of an optically clear and an optically dense solution.

FIG. 4 shows a comparison of the measuring signal in optically clear and optically dense solution. The figure shows how an optically clear solution can be distinguished from an optically dense solution by changing the measuring signals. If an optically dense solution is present in the tube 18, a high proportion of the light irradiated into the medium arrives in light detector 28 and the spectrometer by diffusion. In an optically clear solution, the light is reflected on the rear tube wall 40 or on the inner surface 34 of the lid 16. However, since the optical axes do not meet here, only a part of the irradiated light reaches light detector 28. The total light volume is therefore significantly lower in a clear medium (see FIG. 4). This permits simple and safe differentiation between the different liquid states.

Figure 5:
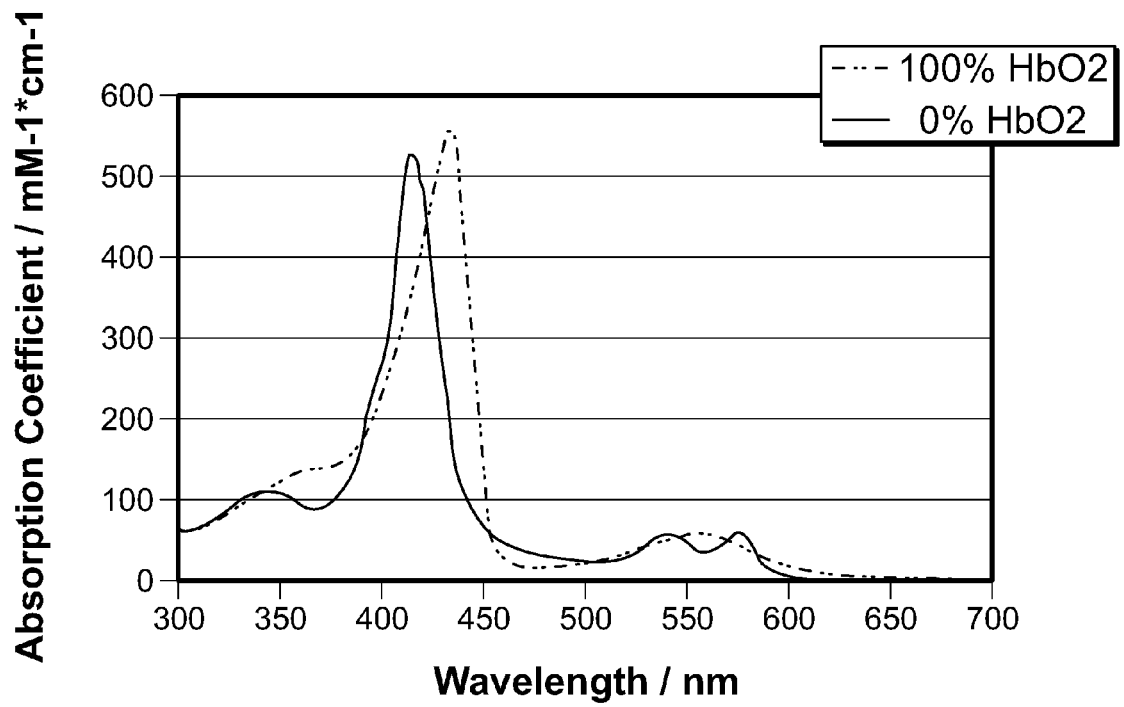
FIG. 5 shows the spectra of hemoglobin for different oxygen saturations.

FIG. 5 shows the spectra of hemoglobin for different oxygen saturations. The colorant of the erythrocytes, the hemoglobin, has slightly different blood spectra at different oxygen saturations. This divergence of the spectra can be compensated during evaluation using the algorithm, as shown below, to ensure precise quantitative measurement.

Figure 6:
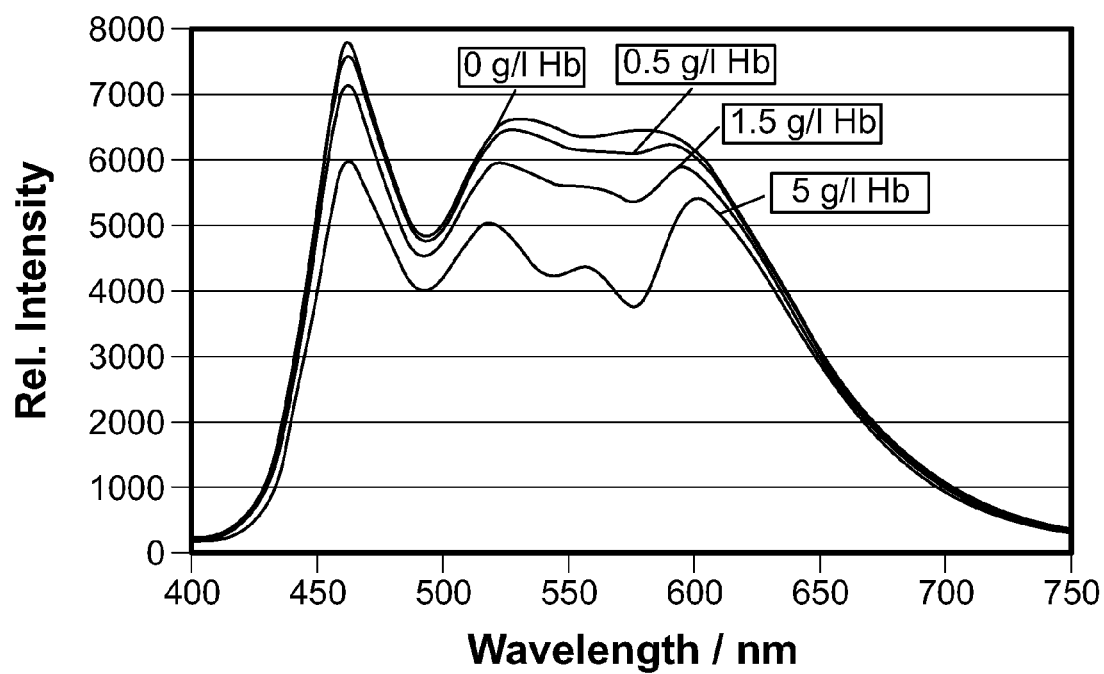
FIG. 6 is a graphic representation of the influence of the hemoglobin concentration to be measured on the measuring signal.

FIG. 6 shows the influence of the hemoglobin concentration to be measured on the measuring signal. By addition of hemoglobin to an optically dense solution, the re-diffused light is reduced in the wavelength range specific to the substance, as shown in FIG. 6. The change of the spectrum in optically clear solution is analogous. Only the total signal before the addition of hemoglobin differs markedly, as shown in FIG. 4. Especially in the 500-600 nm range, the spectra change is very specific due to absorption behavior. This range is applied, for example, in the evaluation algorithm for blood recognition. Overlay in this wavelength range due to marker substances must be taken into account in developing the evaluation algorithm. The hemoglobin peak between 400 and 450 nm can not be used for the evaluation because this peak is strongly overlaid by the bilirubin, which may be included in the liquid 10 as a marker substance in this example.

Figure 7:
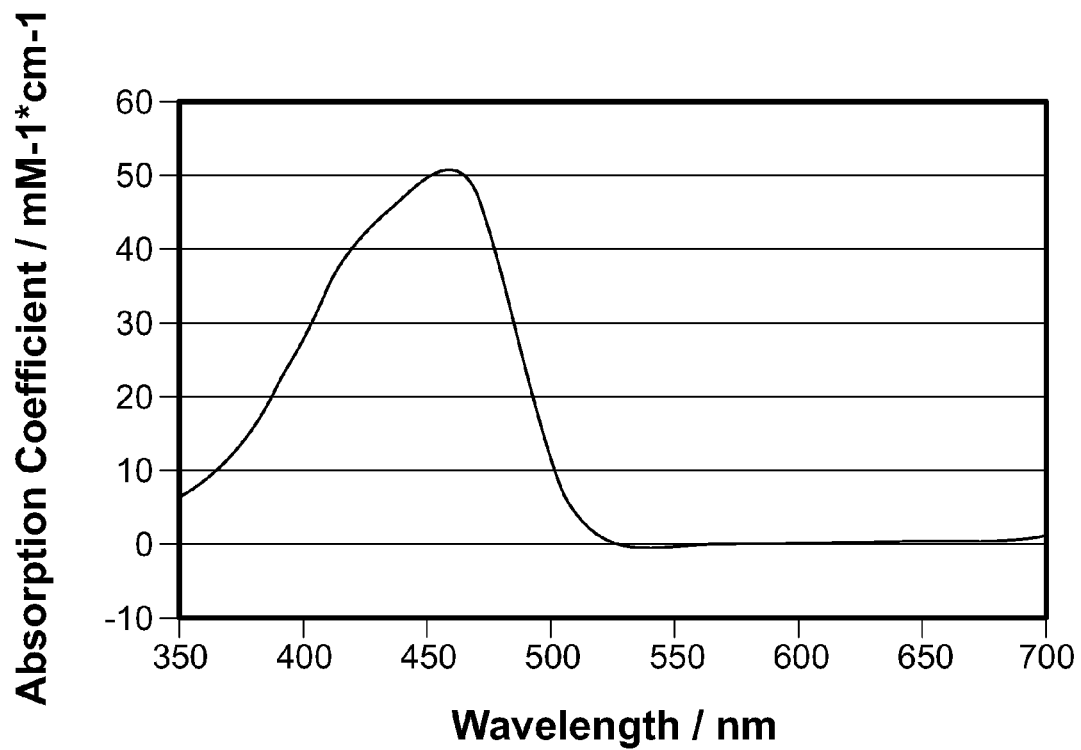
FIG. 7 shows a spectrum of the bilirubin.
Figure 8:
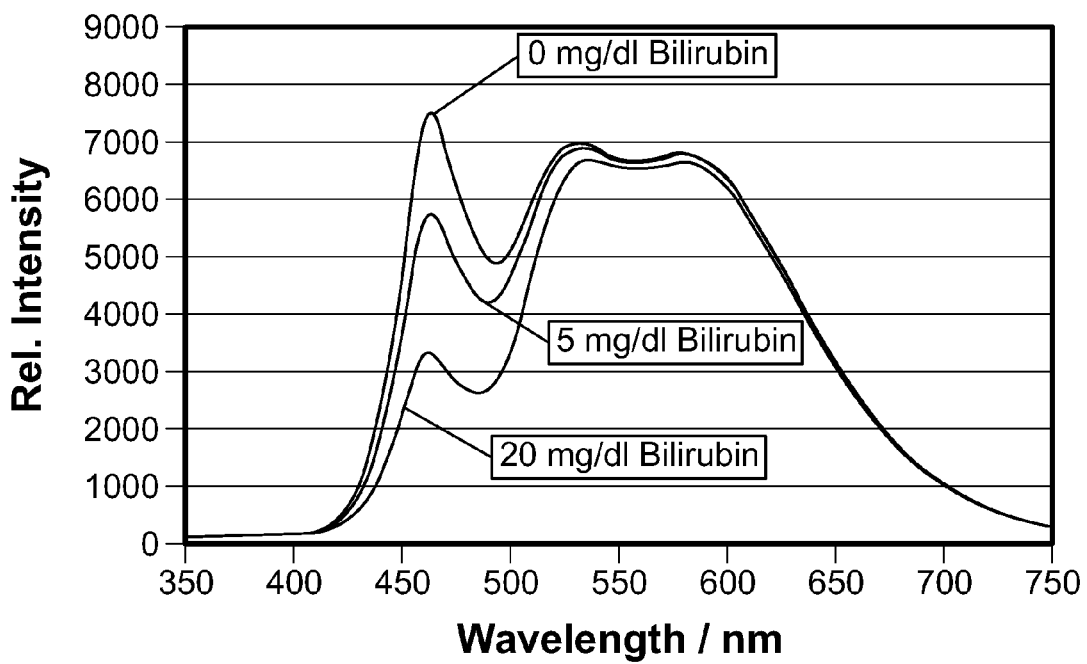
FIG. 8 shows the influence of the bilirubin concentration to be measured on the measuring signal.

The quantitative determination of bilirubin is performed by evaluation of the peak at approximately 450 nm. FIG. 7 shows a spectrum of the bilirubin. FIG. 8 shows the change in the measuring signal or the raw signal due to differing quantities of bilirubin added.

Figure 9:
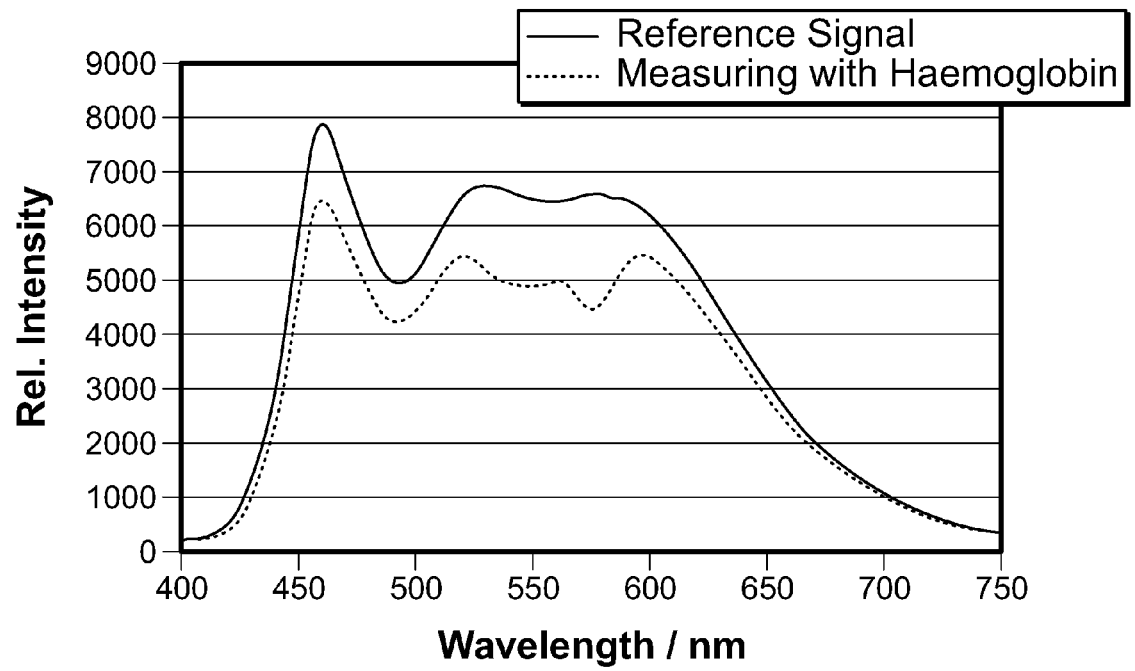
FIG. 9 shows the change of the measuring signal in optically dense solution ("reference signal") by induction of hemoglobin ("measuring signal with hemoglobin").

Distorting influences during analysis as regards hemoglobin are caused, as mentioned above, by substances that have entered the liquid due to the blood purification, such as e.g. bilirubin (see FIGS. 7-8) and by the spectra divergence of the blood at different oxygen saturation levels (see FIG. 5). The evaluation is therefore designed to minimize these distorting influences. Since the light source in the detector is also used for measuring the reference signal, the reference signal is received at a moment in which the tube has been inserted and dummy solution is in the tube. In the case of optically clear solution, this is water or a common salt solution. In the case of an optically dense solution, additional particles are included. FIG. 9 shows a spectrum of the reference signal and a measuring spectrum with hemoglobin in optically dense solution.

To present signal changes compared to the reference signal, the data of the reference spectrum and the measuring spectrum are analyzed according to formula (1).

To provide reliable blood detection, a convolution function is used that may e.g. have the form of equation (2).

To minimize the distorting influence of bilirubin, is has proven sufficient to use the convolution function in a wavelength range from approximately 550 to 700 nm. To form the convolution integral, the signal change function $\Delta S(\lambda)$ is multiplied with the convolution function $\psi(x)$ for every wavelength. The sum of the products then represents the convolution integral for the wavelength $\lambda_0$. If there is no blood in the medium, the convolution should be zero where possible, regardless of all distorting influences. In the presence of blood, on the other hand, it is positive.

To achieve this, $\lambda_0$ must be selected accordingly for a particular convolution function, i.e. it should be the same for saturated and unsaturated blood for this wavelength.

Figure 10:
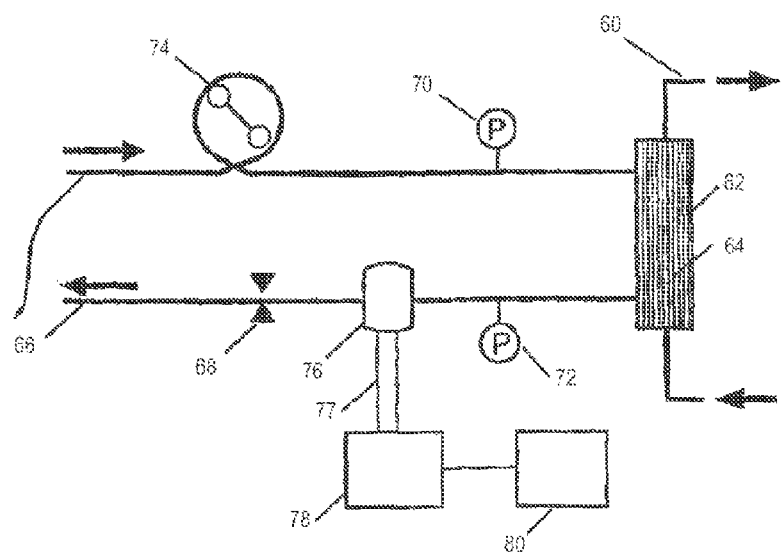
FIG. 10 shows an exemplary flow plan of a blood treatment apparatus with an integrated detector according to the present invention.

FIG. 10 shows a flow plan of a blood treatment apparatus having an integrated detector 76, which corresponds to the detector 8 according to the embodiments of FIGS. 1 to 3. The figure shows a blood circuit 60 from and to a patient and a secondary circuit 66 for blood purification. Both circuits 60 and 66 are connected to a blood treatment unit 62, whereby these circuits are separated within the blood treatment unit 62 by a membrane 64.

In the secondary circuit 66, in which a purification liquid, i.e. a dialysis liquid, is usually pump circulated, the conventional clamps 68, pressure sensors 70 and 72 are located upstream or downstream of the blood treatment unit 62, and a tube pump 74 is interposed upstream of the blood treatment unit 62.

The detector 76 is interposed in the secondary circuit 66 downstream from the blood treatment unit 62, whereby the tube of the secondary circuit 66 forms the tube 18 of the detector 8 according to FIGS. 1-3. As evident from FIG. 10, a spectrometer 78 or another detector, in which the conducted light signals are spectroscopically dispersed, is connected to the detector unit 76 by a light conductor 77.

An analysis unit 80 connected to the spectrometer 78 then analyzes the signal provided by the spectrometer 78, compares the current signal with a reference signal if appropriate, and generates the final signal by means of a computing and discrimination unit (not shown). This final signal can then be conveyed to the main control unit of the blood treatment apparatus (not shown) to be further processed there in an alarm unit.

What is claimed is:

1. A device for measuring stray light in optically dense liquids comprising:
   a casing having at least one flat surface;
   a light-transmissive flexible tube for transporting an optically dense liquid, said flexible tube having a tube wall and being fitted within the casing such that at least one portion of the tube wall is pressed against the at least one flat surface and is thereby flattened;
   a light emitter having a first optical axis, wherein the first optical axis is substantially perpendicular to the at least one flattened portion of the tube wall; and
   a light detector having a second optical axis,
   wherein said light emitter is configured such that light passes through the at least one flattened portion of the tube wall prior to passing into an interior portion of said tube,
   wherein the first optical axis and the second optical axis form an angle of less than about 90°, and
   wherein the intersection of the first optical axis and the second optical axis is located in an area of the interior portion extending from a media boundary between the at least one flattened portion of the tube wall and the optically dense liquid and up to about 0.5 mm into the optically dense liquid.

2. The device of claim 1, wherein the at least one flattened portion of the tube wall is adjacent to the light emitter and the light detector.

3. The device of claim 2, wherein a second flat surface of the casing is adjacent to a second wall of the tube, said surface comprising a reflective surface facing the light emitter and the light detector.

4. The device of claim 1, wherein the first optical axis and the second optical axis form an angle of about 35° to about 55°.

5. The device of claim 1, wherein the first optical axis and the second optical axis form an angle of about 45°.

6. The device of claim 1, wherein the intersection of the first optical axis and the second optical axis is located on a media boundary between the at least one flattened portion of the tube wall and the optically dense liquid.

7. The device of claim 1, further comprising a light-transmissive glass pane disposed between the tube and the light emitter and the light detector.

8. The device of claim 1, wherein the light emitter emits light with a wavelength of about 400 to 700 nm.

9. The device of claim 1, wherein the light detector comprises a light conductor or a light diode.

10. The device of claim 1, wherein the light detector comprises a spectrometer connected with a light conductor.

11. The device of claim 1, further comprising an analysis unit connected to the light detector, the analysis unit calculating a wavelength-dependent signal change function from a wavelength-dependent measuring signal and a wavelength-dependent reference signal, forming a convolution integral from the signal change function for a defined wavelength range, and determining the presence of blood in the optically dense liquid on the basis of the value of the convolution integral.

12. An apparatus for blood treatment comprising a blood treatment unit, a blood circuit connected with the blood treatment unit, and a dialysis liquid circuit connected with the blood treatment unit, whereby the dialysis liquid circuit comprises a tube system and the device of claim 1.

13. A method for the detection of a substance in an optically dense solution comprising:
   providing a flexible light transmissive tube having a tube wall and a measuring device comprising a casing having at least one flat surface,
   fitting the tube in the casing such that at least one portion of the tube wall is pressed against the flat surface and is thereby flattened,
   receiving an optically dense solution in the tube;
   emitting light through the at least one flattened portion of the tube wall along a first optical axis to pass light into an interior portion of the tube;
   receiving light through the tube along a second optical axis, wherein the first optical axis and the second optical axis form an angle of less than about 90° and intersect in an area of the interior portion of the tube extending from a media boundary between the flattened portion of the tube wall and the optically dense solution and up to about 0.5 mm into the optically dense solution;
   measuring the received light as a wavelength-dependent measuring signal;
   calculating a wavelength-dependent signal change function from a wavelength-dependent measuring signal and a wavelength-dependent reference signal;
   forming a convolution integral from the signal change function and a convolution function for a defined wavelength range; and
   determining the presence of the substance on the basis of the value of the convolution integral,
   wherein the substance is chosen from the group consisting of blood, hemoglobin, marker substances, and air.

14. The method of claim 13, wherein the substance is blood.

15. The method of claim 13, wherein the substance is hemoglobin.

16. The method of claim 13, wherein the substance is marker substances.

17. The method of claim 13, wherein the substance is air.

18. The method of claim 13, the measuring device further comprises:
   a light emitter having said first optical axis, wherein the first optical axis is substantially perpendicular to the at least one flattened portion of the tube wall; and
   a light detector having said second optical axis.

19. The method of claim 13, wherein the steps of calculating a wavelength-dependent signal change function, forming a convolution integral, and determining the presence of the substance are performed by an analysis unit.

* * * * *

UNITED STATES PATENT AND TRADEMARK OFFICE
CERTIFICATE OF CORRECTION

| | | |
|---|---|---|
| PATENT NO. | : 8,269,953 B2 | Page 1 of 1 |
| APPLICATION NO. | : 13/241428 | |
| DATED | : September 18, 2012 | |
| INVENTOR(S) | : Bado et al. | |

It is certified that error appears in the above-identified patent and that said Letters Patent is hereby corrected as shown below:

In the Specification

Column 1, line 11, delete "PCT/EP2007/000433" and insert --PCT/EP2007/005631--

Signed and Sealed this
Eighteenth Day of March, 2014

Michelle K. Lee
*Deputy Director of the United States Patent and Trademark Office*